US009971133B2

(12) United States Patent
Akamatsu

(10) Patent No.: US 9,971,133 B2
(45) Date of Patent: May 15, 2018

(54) MULTIREFLECTION CELL, ANALYZER, EXHAUST GAS ANALYZER, AND LIGHT INCIDENT METHOD

(71) Applicant: HORIBA, Ltd., Kyoto (JP)

(72) Inventor: Takeshi Akamatsu, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 0 days. days.

(21) Appl. No.: 15/360,682

(22) Filed: Nov. 23, 2016

(65) Prior Publication Data

US 2017/0168275 A1 Jun. 15, 2017

(30) Foreign Application Priority Data

Dec. 15, 2015 (JP) ................. 2015-244552
Apr. 1, 2016 (JP) ................. 2016-074621

(51) Int. Cl.
*G02B 17/00* (2006.01)
*G01N 21/3504* (2014.01)
(Continued)

(52) U.S. Cl.
CPC .......... *G02B 17/004* (2013.01); *G01J 1/0422* (2013.01); *G01N 21/031* (2013.01);
(Continued)

(58) Field of Classification Search
CPC . G02B 17/004; G02B 17/0636; G01J 1/0422; G01N 21/031; G01N 21/3504; G01N 1/2252; G01M 15/108
(Continued)

(56) References Cited

U.S. PATENT DOCUMENTS 3,726,598 A * 4/1973 Gilby .................. G01N 21/031
356/244
5,065,025 A * 11/1991 Doyle .................. G01N 21/05
250/343
(Continued)

FOREIGN PATENT DOCUMENTS

EP 2388570 A1 11/2011
JP 3268966 B 1/2002
JP 4001857 B 8/2007

OTHER PUBLICATIONS

R. F. Curl and F. K. Tittel, "Tunable infrared laser spectroscopy", Annual Reports Section C (Physical Chemistry) RSC Publishing, 98, pp. 219-272, 2002.*

(Continued)

*Primary Examiner* — Frank Font
(74) *Attorney, Agent, or Firm* — Brooks Kushman P.C.

(57) ABSTRACT

In order to provide a multireflection cell making it possible to decrease the volume of a cell main body into which measurement target gas is introduced as well as reducing the amount of light that is lost without being reflected in a multireflection mechanism, the multireflection cell includes the multireflection mechanism adapted to multiply reflect incident light and then emit the multiply reflected light outward. In addition the multireflection mechanism includes a field mirror, a first objective mirror that faces to the field mirror and is provided on a light incident side in the multireflection mechanism, and a second objective mirror that faces to the field mirror and is provided on a light emitting side in the multireflection mechanism. Further, the light incident into the multireflection mechanism is configured to be first reflected by the second objective mirror.

9 Claims, 10 Drawing Sheets

(51) Int. Cl.
  *G01J 1/04*     (2006.01)
  *G02B 17/06*    (2006.01)
  *G01N 21/03*    (2006.01)
  *G01M 15/10*    (2006.01)
  *G01N 1/22*     (2006.01)

(52) U.S. Cl.
  CPC ..... *G01N 21/3504* (2013.01); *G02B 17/0636* (2013.01); *G01M 15/108* (2013.01); *G01N 1/2252* (2013.01)

(58) Field of Classification Search
  USPC .......... 359/857, 858; 356/244, 437, 300–303
  See application file for complete search history.

(56) References Cited

U.S. PATENT DOCUMENTS

| | | | | |
|---|---|---|---|---|
| 5,604,643 | A * | 2/1997 | Yamamoto | G01N 21/031 359/365 |
| 5,726,752 | A | 3/1998 | Uno et al. | |
| 5,777,735 | A * | 7/1998 | Reagen | G01J 3/453 356/244 |
| 6,723,990 | B2 * | 4/2004 | DiDomenico | G01M 15/108 250/339.01 |
| 9,857,225 | B2 * | 1/2018 | Pearman | G01J 3/453 |
| 2005/0162655 | A1 * | 7/2005 | Nadler | G01N 21/39 356/437 |
| 2013/0003045 | A1 * | 1/2013 | Wilkins | G01J 3/42 356/51 |
| 2013/0335734 | A1 * | 12/2013 | Krause | G01N 21/031 356/246 |
| 2015/0316412 | A1 * | 11/2015 | Bond | G01N 21/39 356/437 |
| 2017/0160136 | A1 * | 6/2017 | Spartz | G01J 3/42 |

OTHER PUBLICATIONS

G. Cleon et al., "Long-cavity Nd:YAG laser used in single-shot spontaneous Raman scattering measurements", Optics Letters, vol. 32, No. 22, Nov. 15, 2007, pp. 3290-3292.*
John U. White, "Long Optical Paths of Large Aperture", Journal of the Optical Society of America, May 1942, vol. 32, pp. 285-288.
EESR dated Feb. 13, 2017 issued for European Patent Application No. 16 199 836.4.
Cleon G et al., Long-Cavity Nd:YAG Laser Used in Single-Shot Spontaneous Raman Scattering Measurements, Optics Letters, vol. 32, No. 22, Nov. 15, 2007, pp. 3290-3292.
Kaur D et al., Multipass Cell for Molecular Beam Absorption Spectroscopy, Applied Optics, vol. 29, No. 1, Jan. 1, 1990, pp. 119-124.

* cited by examiner

CONVENTIONAL TECHNIQUE

MULTIREFLECTION CELL, ANALYZER, EXHAUST GAS ANALYZER, AND LIGHT INCIDENT METHOD

CROSS-REFERENCE TO RELATED APPLICATIONS

This application claims priority to JP Application No. 2015-244552, filed Dec. 15, 2015, and JP Application No. 2016-074621, filed Apr. 1, 2016, the disclosures of which are incorporated in their entirety by reference herein.

TECHNICAL FIELD

The present invention relates to a multireflection cell adapted to multiply reflect incident light and then emit the multiply reflected light outward, and an analyzer using the multireflection cell.

BACKGROUND ART

Gas absorption analysis using, for example, FTIR (Fourier transform infrared) spectroscopy employs a White type multireflection cell having a multireflection mechanism that is configured to include multiple mirrors in order to decrease the required volume of measurement target gas as well as increasing the light path length of light passing through the measurement target gas (see Non-Patent Literature 1).

A multireflection mechanism MR illustrated in FIG. 9 is arranged inside a cell main body (not illustrated in FIG. 9) into which measurement target gas is introduced. Also, the multireflection mechanism MR includes: one field mirror 12; a first objective mirror 13 that faces to the field mirror 12 and is provided on a light incident side in the multireflection mechanism MR; and a second objective mirror 14 that faces to the field mirror 12 and is provided on a light emitting side in the multireflection mechanism MR.

Into such a multireflection mechanism MR, light having a predetermined spread with respect to a light axis is introduced so as to be first reflected by the first objective mirror 13. After that, the introduced light is repeatedly reflected between the field mirror 12 and the first or second objective mirror 13 or 14. The light repeatedly reflected in the multireflection mechanism MR is finally emitted outward from the emitting side that is set on the side opposite to the light incident side in the multireflection mechanism MR.

Meanwhile, when desiring to measure a time change of a component of measurement target gas, such as to analyze exhaust gas of an engine, it is demanded to improve responsiveness by decreasing the volume of the cell main body to minimize a time to replace the measurement target gas to be introduced.

When decreasing the volume of the cell main body in order to respond to the demand, the interval between the opposite mirrors is inevitably shortened. For this reason, in order to achieve measurement accuracy comparable to conventional one, it is necessary to increase the number of times of light reflection in the multireflection mechanism MR to keep a light path length comparable to a conventional length.

However, when increasing the number of times of reflection in the multireflection mechanism MR, reflection points are more densely concentrated in the vicinity of the outer edge of the field mirror 12 than the central part. As a result, reflection points are overlapped near an emitting port OP in the vicinity of the outer edge, and part of the light may be emitted outward from the multireflection mechanism MR before reaching a prescribed number of times of reflection (see FIG. 8). For this reason, the absorbance of the measurement target gas cannot be accurately measured.

CITATION LIST

Patent Literature

Non-Patent Literature 1: Long Optical Paths of Large Aperture, Journal of the Optical Society of America, May, 1942, Vol. 32

SUMMARY

Technical Problem

The present invention is made in consideration of the above-described problem, and intends to provide a multireflection cell that makes it possible to decrease the volume of a cell main body into which measurement target gas is introduced, and reduce the amount of light that is emitted outward before reaching a prescribed number of times of reflection in a multireflection mechanism and lost without being reflected.

Solution to Problem

That is, the multireflection cell according to the present invention is a multireflection cell including a multireflection mechanism adapted to multiply reflect incident light and then emit the multiply reflected light outward, and the multireflection mechanism includes: a field mirror; a first objective mirror that faces to the field mirror and is provided on a light incident side in the multireflection mechanism; and a second objective mirror that faces to the field mirror and is provided on a light emitting side in the multireflection mechanism. In addition, the light incident into the multireflection mechanism is configured to be first reflected by the second objective mirror.

Also, a light incident method according to the present invention is a method making light incident into a multireflection cell including a multireflection mechanism adapted to multiply reflect the incident light and then emit the multiply reflected light outward, and the multireflection mechanism includes: a field mirror; a first objective mirror that faces to the field mirror and is provided on a light incident side in the multireflection mechanism; and a second objective mirror that faces to the field mirror and is provided on a light emitting side in the multireflection mechanism. In addition, the light is made incident into the multireflection mechanism such that the light incident into the multireflection mechanism is first reflected by the second objective mirror.

Such configurations make it possible to increase the incident angle of the light incident into the multireflection mechanism, and therefore contrary to before, it can be adapted to densely concentrate reflection points in the central part of the field mirror, but in the outer edge part of the field mirror at least on the light emitting side, not to concentrate reflection points so much. Note that the central part of the field mirror refers to a concept indicating an area that includes at least the central part and is away from a light emitting port side, and the outer edge part of the field mirror refers to a concept indicating an area near the light emitting port side.

Accordingly, even when downsizing the multireflection cell, and increasing the number of times of reflection to increase the light path length of the light passing through measurement target gas, the amount of light that is emitted outward before reaching a prescribed number of times of reflection, which is caused by the overlap of reflection points in the outer edge part of the field mirror on the light emitting side, can be reduced. For this reason, for example, a response speed at the time of absorption analysis can be improved, and at the same time the measurement accuracy of the absorption analysis can be kept high.

More specifically, the conventional multireflection cell is configured to make light incident such that the light is first reflected by the first objective mirror arranged on the incident side in the multireflection mechanism, and emit light resulting from final reflection by the second objective mirror outward. For this reason, the light axis of a light beam from the second objective mirror to, for example, the emitting port formed in the field mirror forms only a small angle with respect to the light axis of the field mirror, and this has been the cause for the concentration of reflection points near the emitting port. On the other hand, the multireflection cell according to the present invention is configured to be able to make the light first incident on the second objective mirror far away from the incident side of the multireflection mechanism and emit light resulting from final reflection by the first objective mirror outward. For this reason, light traveling from the second objective mirror to the field mirror, and light traveling from the field mirror to the first objective mirror travel more obliquely than before with respect to the light axis of the field mirror, and the incident angle of light from the first objective mirror to the field mirror can be increased. As a result, reflection points can be prevented from being concentrated near the emission port of the multireflection mechanism to increase density, and light emitted outward before the number of times of reflection does not reach the predetermined number of times can be easily prevented.

In order to make it possible to configure the multireflection mechanism using a requisite minimum number of mirrors, facilitate the downsizing of the multireflection cell, and provide a high performance analyzer, it is only necessary that the first objective mirror and the second objective mirror are arranged symmetrically with respect to a symmetry plane including the light axis of the field mirror.

In order to make it easy to increase the number of times of light reflection in the multireflection mechanism and reduce the amount of light emitted outward before reaching the prescribed number of times of reflection when the multireflection cell is downsized, it is only necessary that the curvature center of the first objective mirror is set on a light emitting side of the field mirror in the multireflection mechanism; and the curvature center of the second objective mirror is set on a light incident side of the field mirror in the multireflection mechanism.

Specific configurations for making it possible to eliminate the need to make light incident from between the field mirror and the first objective mirror, decrease the internal volume of the multireflection cell, and reduce the amount of light emitted outward before reaching the prescribed number of times of reflection include one in which the field mirror includes: a light incident port through which the light is incident from outside the multireflection mechanism; and a light emitting port through which the light is emitted outward from the multireflection mechanism. Such a configuration makes it possible to emit light repeatedly reflected in the multireflection mechanism outward of the multireflection mechanism through the light emitting port before reaching the outer edge of the field mirror. Accordingly, the number of reflection points in the outer edge part can be reduced to reduce light not reflected by any mirror.

Specific configuration examples for making it possible to increase the number of times of reflection to increase a light path length and reduce the amount of light emitted outward before reaching the prescribed number of times of reflection include one in which the arrangement interval between adjacent ones of multiple reflection points formed on a reflecting surface of the field mirror is configured to be larger in the outer edge part of the reflecting surface than the central part.

Specific configuration examples making it possible to reduce the occurrence density of reflection points in the outer edge part of the field mirror and reduce the amount of light emitted outward before reaching the prescribed number of times of reflection include one in which an array of multiple reflection points formed on a reflecting surface of the first objective mirror and an array of multiple reflection points formed on a reflecting surface of the second objective mirror respectively draw parabolas, and vertexes of the respective parabolas are configured to face outward of the multireflection mechanism.

The multireflection cell includes a cell main body adapted to contain the multireflection mechanism. Also, on the side of the field mirror in the cell main body, an incident window allowing the light to be incident into the multireflection mechanism from outside and an emitting window allowing the light to be emitted outward from the multireflection mechanism are provided. In this configuration, in order to reduce a loss due to light reflection at the incident window and the emitting window, it is desirable that a face plate part of the incident window is orthogonal to the light axis of the incident light and faces to the side of the second objective mirror; and a face plate part of the emitting window is orthogonal to the light axis of the emitting light and faces to the side of the first objective mirror.

Also, in order to reduce the loss due to the light reflection at the incident window and the emitting window, it is desirable that on the surfaces of the incident window and the emitting window, an antireflection film is formed.

When light finally reflected by the first objective mirror is configured to be emitted outward from the multireflection mechanism, the light can be led outward from an area on the field mirror where the formation density of reflection points is small, and light emitted outward without being reflected the predetermined number of times can be eliminated to easily prevent a light amount loss.

An analyzer using the multireflection cell according to the present invention makes it possible to decrease the internal volume of the multireflection cell to increase measurement responsiveness and at the same time, reduce light emitted outward before reaching the predetermined number of times of reflection to provide analysis with high measurement accuracy.

An exhaust gas analyzer including the multireflection cell according to the present invention in which exhaust gas is configured to exist between the field mirror, and the first objective mirror and the second objective mirror makes it possible to perform component analysis and concentration measurement of the exhaust gas with high accuracy even though being wholly downsized.

Advantageous Effects of Invention

As described above, the multireflection cell of the present invention is configured such that the light incident into the multireflection mechanism is first reflected by the second objective mirror, and therefore reflection points on the field mirror can be concentrated in the central part and made sparse in the outer edge part. As a result, even when downsizing the multireflection cell, and increasing the number of times of reflection in the multireflection mechanism in order to increase a light path length, light emitted outward before reaching the prescribed number of times of reflection can be reduced to keep measurement accuracy high. Reflection light from an objective mirror can be preferably prevented from being emitted outward in the outer edge part of the field mirror before reaching the prescribed number of times of reflection.

DESCRIPTION OF EMBODIMENTS

A multireflection cell 100 and analyzer 200 according to one embodiment of the present invention will be described with reference to FIG. 1.

The analyzer 200 of the present embodiment is used to measure the concentrations of multiple components contained in exhaust gas discharged from an internal combustion engine of an automobile as pieces of time series data. That is, the analyzer 200 of the present embodiment is configured as an exhaust gas analyzer.

Figure 1:
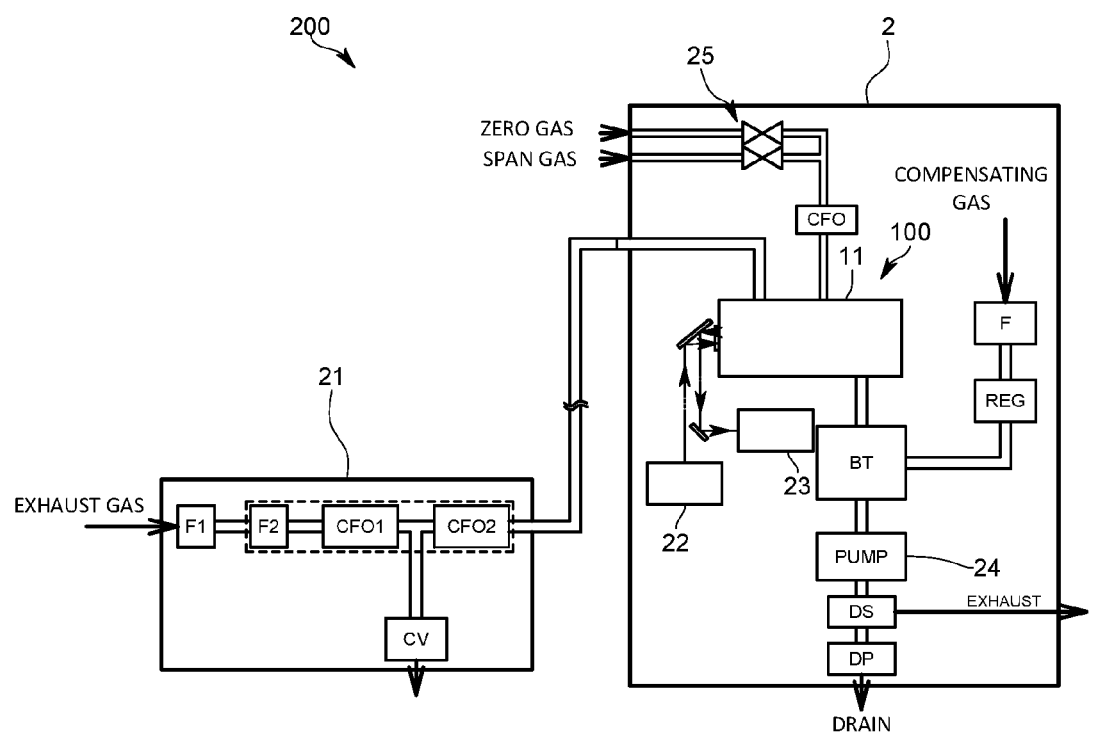
FIG. 1 is a schematic diagram illustrating an analyzer according to one embodiment of the present invention.

As illustrated in FIG. 1, the analyzer 200 includes: a dilution mechanism 21 that is connected to the tail pipe of the automobile to sample part of the exhaust gas as well as diluting the sampled exhaust gas to a predetermined concentration with air; and an analysis mechanism 2 that is connected to the dilution mechanism 21 and measures the concentrations of the respective components in the exhaust gas from the diluted exhaust gas.

The analysis mechanism 2 is one adapted to measure the respective concentrations of the multiple components in the exhaust gas, such as CO2 and NOX, using the FTIR method. The analysis mechanism 2 includes: the multireflection cell 100 into which the diluted exhaust gas resulting from the dilution by the dilution mechanism 21 is introduced; a light source 22 adapted to introduce infrared light into the multireflection cell 100; a light detector 23 adapted to detect the intensity of light emitted through the multireflection cell 100; a pump 24 adapted to introduce the diluted exhaust gas into the multireflection cell 100; and a reference gas supply part 25 adapted to supply zero gas and span gas for calibrating the light detector 23 into the multireflection cell 100. Note that the pump 24 may be provided upstream or downstream of the multireflection cell 100.

Next, the details of the multireflection cell 100 will be described.

The multireflection cell 100 includes: a cell main body 11 into which the diluted exhaust gas as measurement target gas is introduced; and a multireflection mechanism MR that is provided in the cell main body 11 and multiply reflects the incident light and then emit the multiply reflected light outward.

Figure 2:
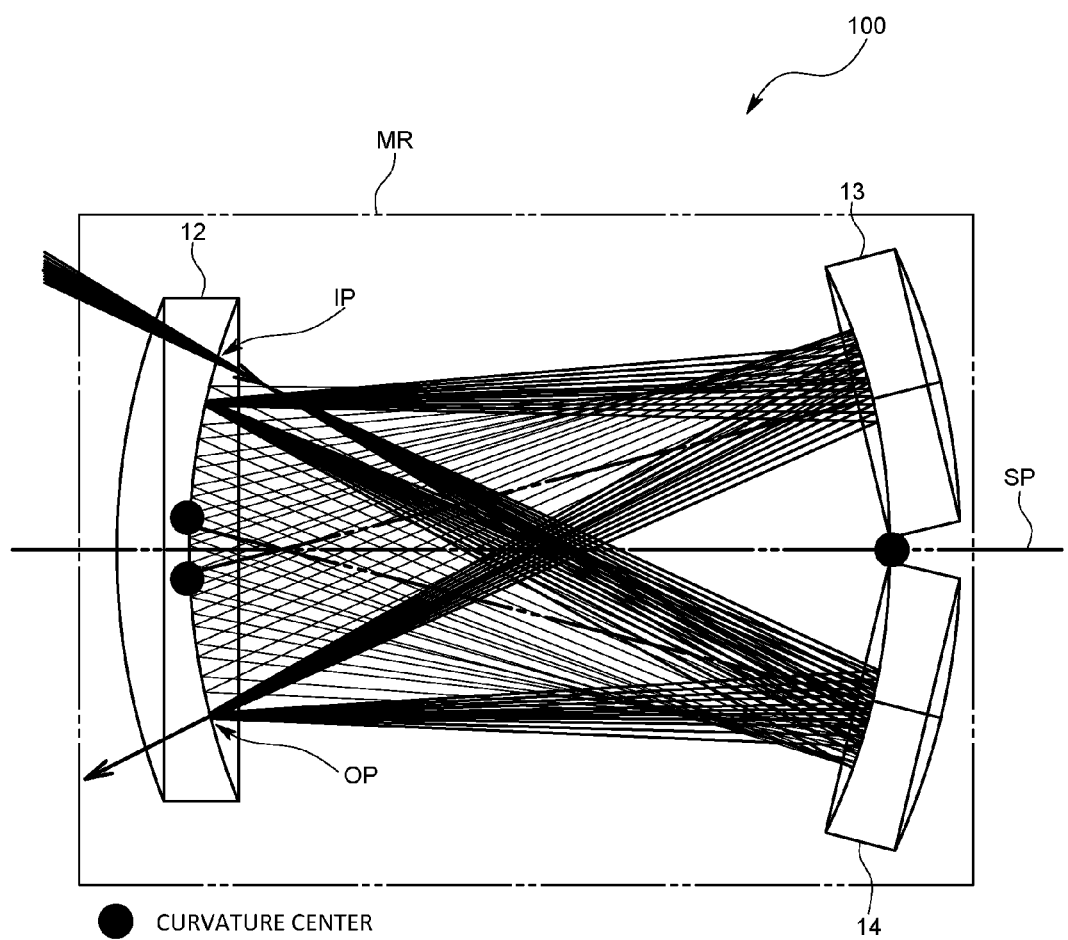
FIG. 2 is a schematic diagram illustrating a multireflection cell in the same embodiment.

As illustrated in FIG. 2, the multireflection mechanism MR includes: one field mirror 12; and first and second objective mirrors 13 and 14 provided so as to face to the field mirror 12. Each of the mirrors is a concave mirror, and arranged so as to image reflecting light on the reflecting surface of an opposite mirror. More specifically, the first objective mirror 13 and the second objective mirror 14 are arranged so as to be symmetrical (plane-symmetrical) with respect to a symmetry plane SP (a virtual plane passing through the centerline of the reflection cell) including the light axis of the field mirror 12. Note that in the following description, "a light incident side in the multireflection mechanism MR" and "a light emitting side in the multireflection mechanism MR" are defined with the symmetry plane SP as a boundary. That is, in FIG. 2, the upper half with respect to the symmetry plane SP into which the infrared light emitted from the light source 22 is incident corresponds to the light incident side in the multireflection mechanism MR. Also, in FIG. 2, the lower half with respect to the symmetry plane SP corresponds to the light emitting side in the multireflection mechanism MR. In the present embodiment, the first objective mirror 13 is arranged on the light incident side in the multireflection mechanism MR, and the second objective mirror 14 is arranged on the light emitting side in the multireflection mechanism MR.

The field mirror 12 is provided in the cell main body 11 at the end on a side where the light from the light source 22 is introduced. Also, the curvature radius of the reflecting surface of the field mirror 12 is set to be substantially the same as those of the first and second objective mirrors 13 and 14. In the field mirror 12, a light incident port IP that is a penetrating opening for introducing the infrared light into the multireflection mechanism MR, i.e., into between the field mirror 12 and the first or second objective mirror 13 or 14 is formed on the light incident side in the multireflection mechanism MR. Also, in the field mirror 12, a light emitting port OP that is a penetrating opening for emitting outward the light multiply reflected in the multireflection mechanism MR is formed in a position symmetrical to the light incident port IP with respect to the symmetry plane SP.

The light axis direction of the infrared light incident through the light incident port IP is adapted to cross the central part of the reflecting surface of the second objective mirror 14 arranged on the light emitting side in the multireflection mechanism MR. That is, the infrared light emitted from the light source 22 but not yet multiply reflected is configured to be first incident on and reflected by the reflecting surface of the second objective mirror 14 in the multireflection mechanism MR. In other words, the light having passed through the light incident port IP is adapted to be first incident on the objective mirror on a far side as viewed from the light incident port IP. In still other words, the light incident into the multireflection mechanism MR is configured to be incident on the second objective mirror 14 after passing through the symmetry plane SP including the light axis of the field mirror 12.

The orientations of the first and second objective mirrors 13 and 14 are set such that virtual straight lines connecting the centers of the curvature radii and the centers of the reflecting surfaces cross the symmetry plane SP, respectively and correspondingly. That is, the first objective mirror 13 arranged on the light incident side in the multireflection mechanism MR is adapted to face to the light emitting side of the field mirror 12. On the other hand, the second objective mirror 14 arranged on the light emitting side in the multireflection mechanism MR is adapted to face to the light incident side of the field mirror 12. The curvature centers of the first and second mirrors 13 and 14 are respectively arranged near the reflecting surface of the field mirror 12.

The trajectory of a light beam and the characteristics of reflection points in the multireflection cell 100 configured as described above will be described while being compared with conventional ones.

Figure 3:
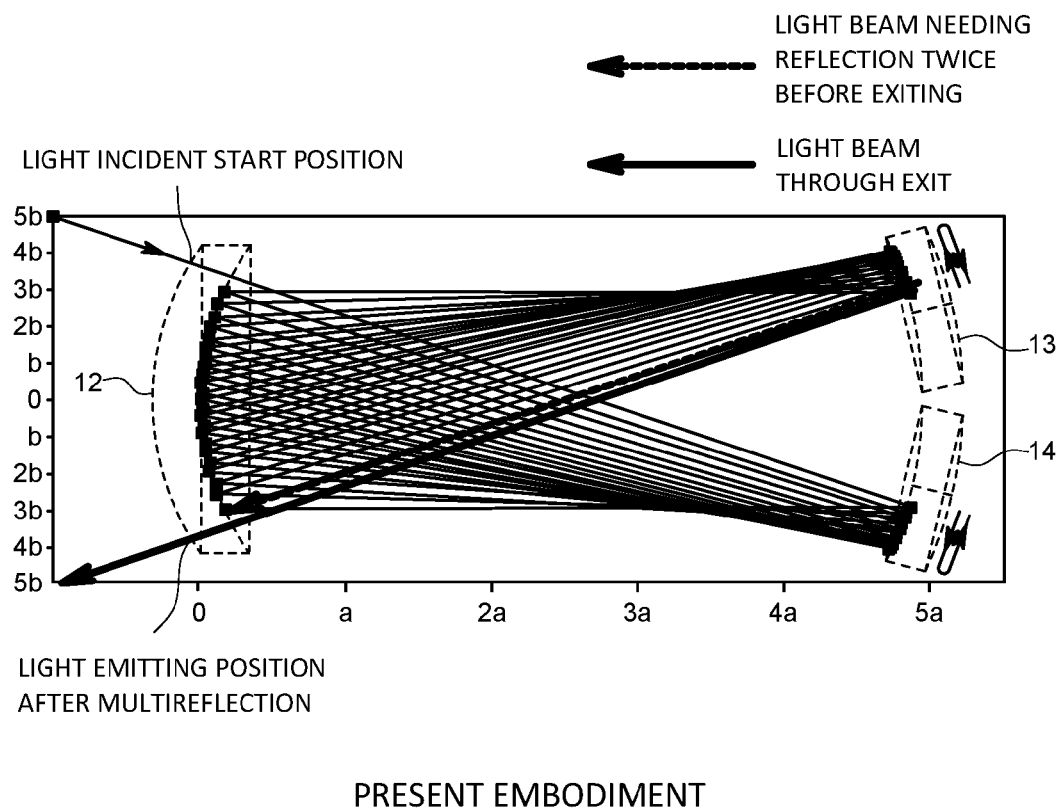
FIG. 3 is a schematic diagram illustrating a reflection state in the multireflection cell in the same embodiment.

FIG. 3 illustrates the trajectory of the light obtained when the light is incident into the multireflection cell 100 of the present embodiment. Also, FIG. 4 is a diagram illustrating the extract of only the trajectory of the light immediately after the incidence and also illustrating reflection point occurrence states of the respective mirrors in the present embodiment.

Figure 7:
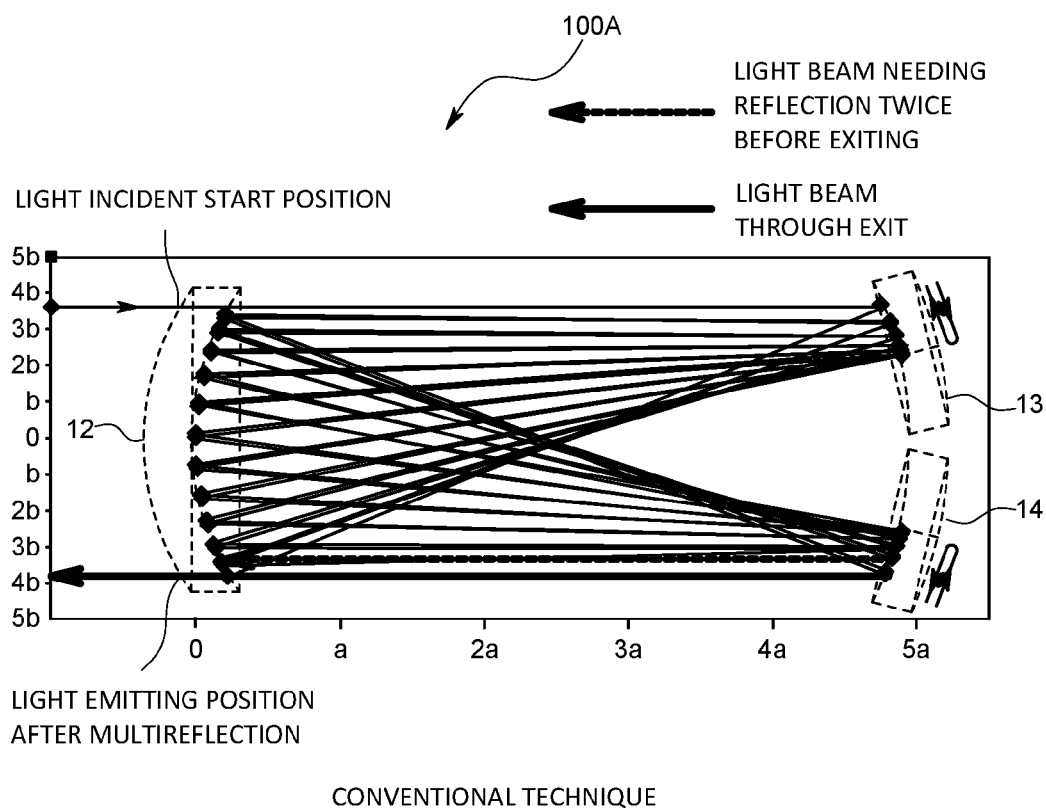
FIG. 7 is a schematic diagram illustrating a reflection state in a conventional multireflection cell.

On the other hand, FIG. 7 illustrates the trajectory of the light obtained when the light is made incident on the first objective mirror 13 near the light incident port IP as in a conventional case. Also, FIG. 8 is a diagram illustrating the extract of only the trajectory of the light immediately after the incidence and also illustrating reflection point occurrence states of the respective mirrors in the conventional case.

Figure 4:
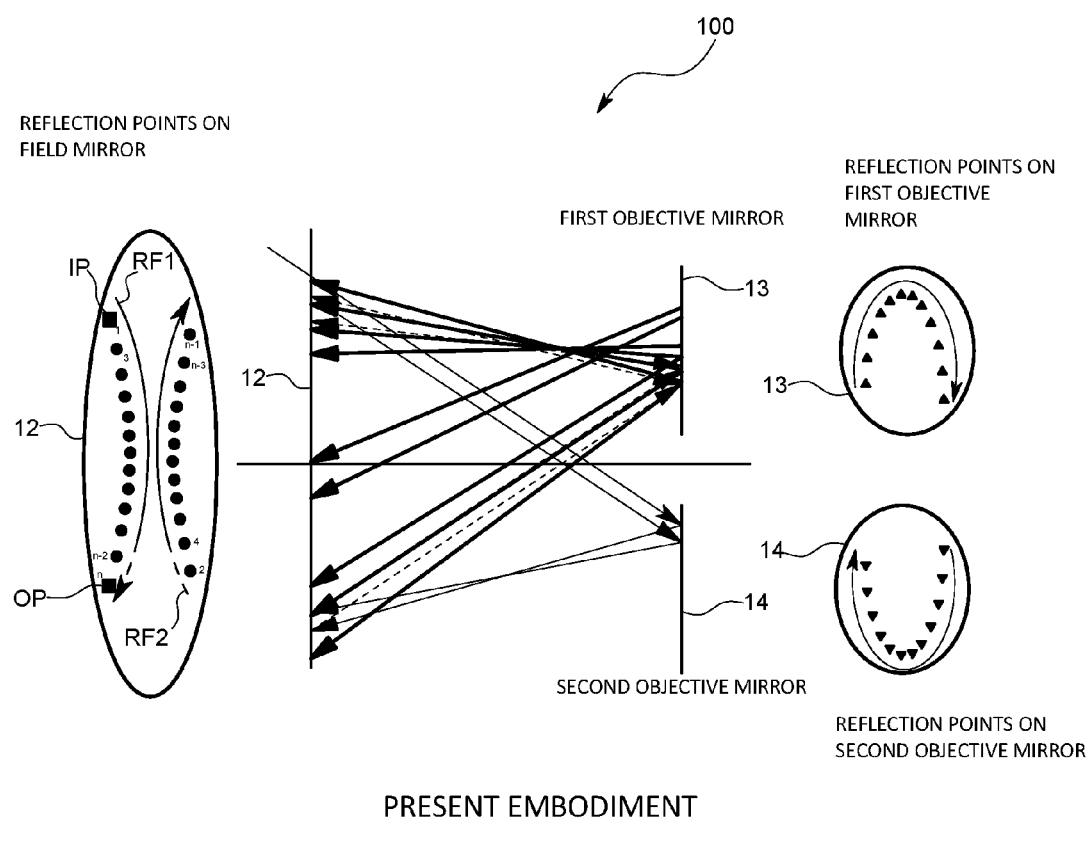
FIG. 4 is a schematic diagram illustrating reflection point intervals in the multireflection cell of the same embodiment.

As illustrated in FIGS. 3 and 4, when the light is made incident on the second objective mirror 14 far from the light incident port IP, light reflection is repeated in the order of the second objective mirror 14, field mirror 12, first objective mirror 13, field mirror 12, second objective mirror 14, and field mirror 12. Further, when focusing on reflection points formed on the reflecting surface of the field mirror 12, as indicated by numbers and arrows in FIG. 4, a reflection point formed by the trajectory RF1 of reflection light from the first objective mirror 13 moves from the light incident port IP toward the light emitting port OP as the reflection is repeated. Also, a reflection point formed by the trajectory RF2 of reflection light from the second objective mirror 14 moves from the light emitting port OP toward the light incident port IP as the reflection is repeated. In any of the cases, in the outer edge part of the field mirror 12, the occurrence interval between adjacent reflection points is sparse as compared with that in the central part. Accordingly, even when increasing the number of times of reflection, reflection points can be prevented from being overlapped and concentrated in the vicinity of the light emitting port OP formed in the outer edge part of the field mirror 12. For this reason, a reflection point of light necessary to be reflected, for example, two times that are left before reaching a prescribed number of times of reflection can be kept sufficiently far from the vicinity of the light emitting port OP, and therefore the light not reaching the prescribed number of times of reflection can be prevented from being emitted outward through the light emitting port OP. This is because since the light is made incident on the second objective mirror 14 far from the light incident port IP, the incident angle of the light with respect to the field mirror 12 is large in the outer edge part.

Figure 8:
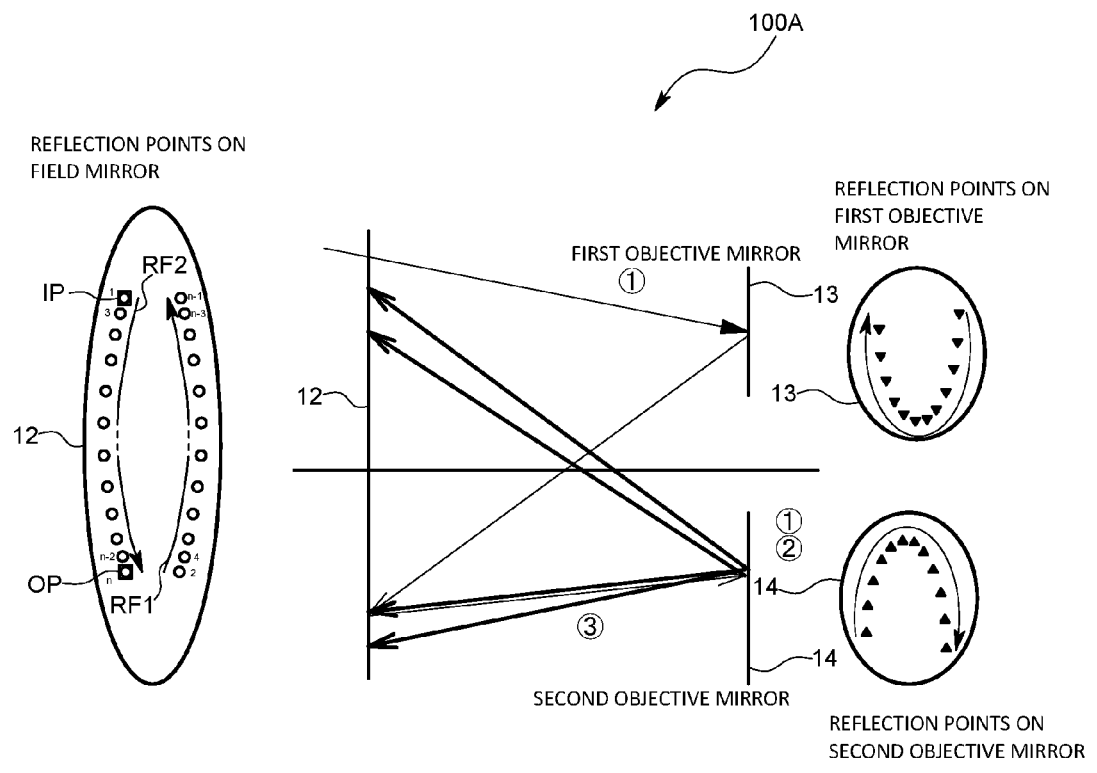
FIG. 8 is a schematic diagram illustrating reflection point intervals in the conventional multireflection cell.

On the other hand, in the conventional technique illustrated in FIGS. 7 and 8, a tendency directly opposite to the reflection point occurrence state of the field mirror 12 in the present embodiment appears.

As illustrated in FIGS. 7 and 8, when the light is made incident on the first objective mirror 13 near the light incident port IP, light reflection is repeated in the order of the first objective mirror 13, field mirror 12, second objective mirror 14, field mirror 12, first objective mirror 13, and field mirror 12. Further, when focusing on reflection points formed on the reflecting surface of the field mirror 12, as a result of making the light incident on the first objective mirror 13 near the light incident port IP, a reflection point formed by the trajectory RF1 of reflection light from the first objective mirror 13 moves from the light emitting port OP toward the light incident port IP as the reflection is repeated. Also, a reflection point formed by the trajectory RF2 of reflection light from the second objective mirror 14 moves from the light incident port IP toward the light emitting port OP as the reflection is repeated. In any of the cases, in the outer edge part of the field mirror 12, the occurrence interval between adjacent reflection points is dense as compared with that in the central part. This is because the incident angle of the light with respect to the field mirror 12 is small in the outer edge part.

As a result, as illustrated in FIG. 7, in the outer edge part of the field mirror 12, the interval between adjacent reflection points is shortened, and therefore reflection points are concentrated. In particular, when the light is not one having high coherency such as laser light but light having a predetermined spread with respect to the light axis, the concentration of reflecting points in the vicinity of the light emitting port OP allows the light spreading with respect to the light axis to enter the light emitting port OP before reaching the prescribed number of times of reflection. For this reason, as the number of times of reflection in the outer edge part increases, the amount of light that emitted outward of the multireflection mechanism MR without reaching the prescribed number of times of reflection is increased.

Further, as illustrated in FIG. 4, in the present embodiment, the array of multiple reflection points formed on the reflecting surface of the first objective mirror 13 and the array of multiple reflection points formed on the reflecting surface of the second objective mirror 14 respectively form discrete curves having peaks. These discrete curves are substantially parabolic, and on the first objective mirror 13, the discrete curve is formed so as to be convex on the light incident side in the multireflection mechanism MR, whereas on the second objective mirror 14, the discrete curve is forms so as to be convex on the light emitting side in the multireflection mechanism MR.

As described, in the multireflection cell 100 of the present embodiment, the light is adapted to be first incident on the second objective mirror 14 arranged on the light emitting side of the multireflection mechanism MR, and therefore as described above, on the field mirror 12, a reflection frequency in the outer edge part can be decreased whereas a reflection frequency in the central part can be increased.

Accordingly, even in the case where the light incident into the multireflection cell 100 has low coherency and travels while spreading at a predetermined solid angle, the amount of light that enters the light emitting port OP before reaching the prescribed number of times of reflection in the outer edge part of the field mirror 12 and emits outward can be reduced.

In other words, in the conventional light incident configuration, when simply decreasing the volume of the multireflection cell 100, a reflection frequency in the outer edge part of the field mirror 12 increases to increase the amount of light emitted outward before reaching the prescribed number of times of reflection, and therefore absorption necessary to perform the FTIR method cannot be sufficiently achieved. On the other hand, in the present embodiment, even when downsizing the multireflection cell 100, light having an amount enough to ensure analysis accuracy can be emitted from the multireflection cell 100. Accordingly, the replacement speed of the measurement target gas in the multireflection cell can be increased by decreasing the volume. As a result, a component analysis response speed can be increased and at the same time component analysis with substantially the same accuracy as before can also be performed.

Other embodiments will be described.

The analyzer of the above embodiment is one adapted to analyze the exhaust gas, but may be one adapted to perform measurement on another gas on the basis of absorbance. For example, the present invention may be used for measurement based on, for example, an NDIR method or the like. Also, in the case of measurement using absorptiometry, the multireflection cell of the present invention makes it possible to achieve both high measurement responsiveness and accuracy. Further, the multireflection cell can also be used for other than the analyzer based on absorbance measurement.

Figure 9:
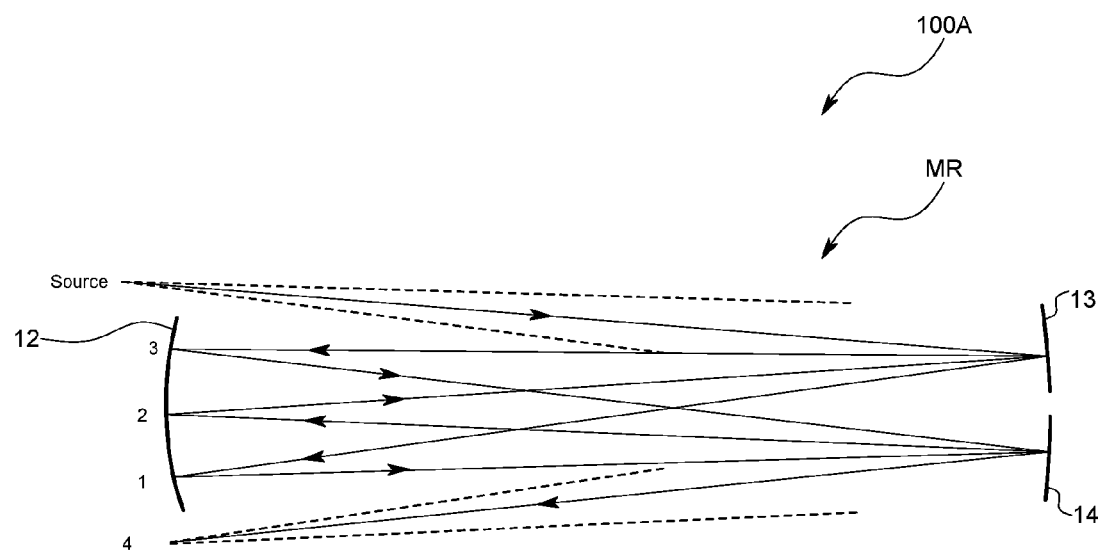
FIG. 9 is a schematic diagram illustrating a point on a first objective mirror at which light is made incident in the conventional multireflection cell.

The above embodiment is configured to make the light incident on the second objective mirror through the light incident port provided in the field mirror, but for example, as with a conventional example illustrated in FIG. 9, may be adapted to make the light incident into the multireflection mechanism from between the field mirror and the first objective mirror, and make the light first incident on and reflected by the second mirror. Even in such a configuration, substantially the same effect as that of the above embodiment can be obtained.

The numbers of field mirrors and objective mirrors are not limited to those described in the above embodiment. Multiple mirrors may be additionally provided. In such a case, it is only necessary to configure the light not to be made first incident on an objective mirror nearest the incident side of the multireflection mechanism but to be made first incident on and reflected by another objective mirror. That is, the definition of the light incident side or the light emitting side in the multireflection mechanism is not limited to the one that as described in the above embodiment, is given with the symmetry plane determined on the basis of the light axis of the field mirror as a reference. For example, when three objective mirrors are provided side by side in the light traveling direction in the multireflection mechanism, the light incident side and the light emitting side may be defined with a virtual plane set between the first objective mirror and the second objective mirror as a reference. In this case, it is only necessary to configure the light to be first incident on any of the second objective mirror and the third objective mirror.

Figure 5:
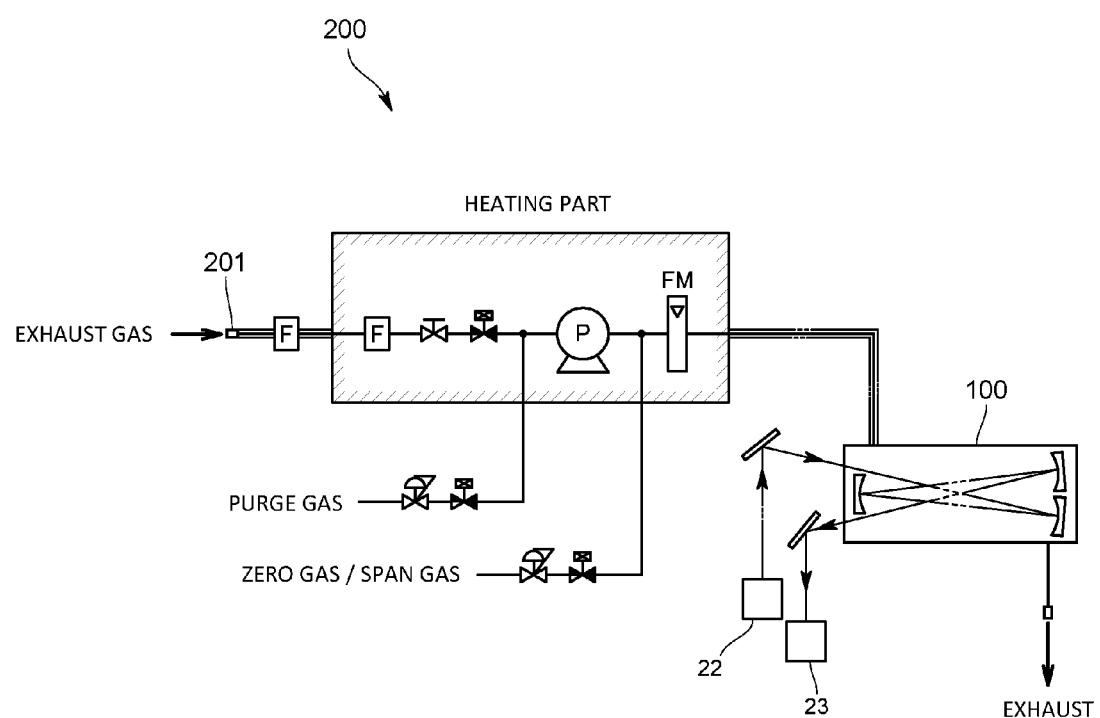
FIG. 5 is a schematic diagram illustrating an analyzer according to a variation.

In the above embodiment, the sampled exhaust gas is diluted with air. However, as illustrated in FIG. 5, the analyzer 200 may be, for example, one adapted to sample a part or the whole of exhaust gas discharged from the tail pipe of an automobile by a sample sampling part 201 and introduce the exhaust gas sampled by the sample sampling part 201 into the multireflection cell 100 without diluting the sampled exhaust gas.

Figure 6:
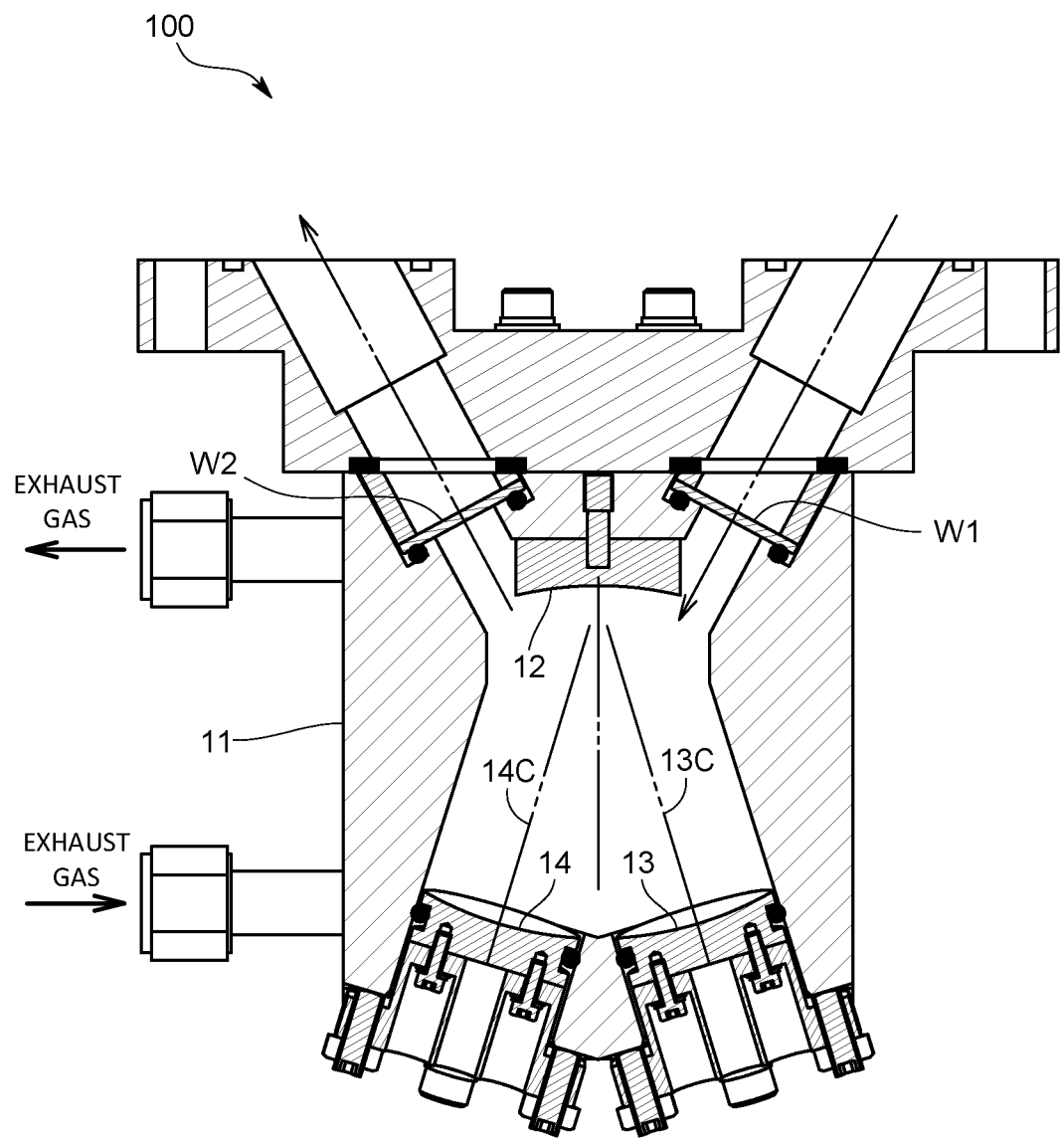
FIG. 6 is a schematic diagram illustrating a multireflection cell in another variation.

Further, as illustrated in FIG. 6, it may be adapted to, on the field mirror 12 side in the cell main body 11, provide an incident window W1 for making light incident into the multireflection mechanism MR from outside and an emitting window W2 for emitting light outward from the multireflection mechanism MR. In addition, for the incident window W1 and the emitting window W2, the use of a substrate such as a barium fluoride ($BaF_2$) substrate, zinc selenide (ZnSe) substrate, or zinc sulfide (ZnS) substrate is conceivable.

Note that the incident window W1 is tilted with respect to the light axis of the field mirror 12 facing to the second objective mirror 14 side. That is, the incident window W1 faces to the reflecting surfaces of the second objective mirror 14, and is arranged such that the normal direction of the incident window W1 substantially coincides with the light axis 14C of the second objective mirror 14. Also, the emitting window W2 is tilted with respect to the light axis of the field mirror 12 facing to the first objective mirror 13 side. That is, the emitting window W2 faces to the reflecting surface of the first objective mirror 13, and is arranged such that the normal direction of the emitting window W2 substantially coincides with the light axis 13C of the first objective mirror 13. In other words, face plate parts of the incident window W1 and the emitting window W2 are arranged so as to be perpendicular to the light axes of the incident light and emitting light, and also so as to face to the second objective mirror 14 and the first objective mirror 13, respectively.

Further, in order to reduce a loss due to light reflection at the incident window W1 and the emitting window W2, an antireflection film is formed on the surfaces of the incident window W1 and the emitting window W2. The antireflection film is one having a transmittance of 80% or more in an infrared wavelength range used for the analysis. Also, the antireflection film may be formed on both or any ones of the cell inside surfaces and cell outside surfaces of the incident window W1 and the emitting window W2. Note that when forming the antireflection film on the cell inside surfaces causes a problem of corrosion due to the exhaust gas or a problem of contamination of the exhaust gas due to the antireflection film, it is desirable to provide the antireflection film only on the cell outside surfaces.

Figure 10:
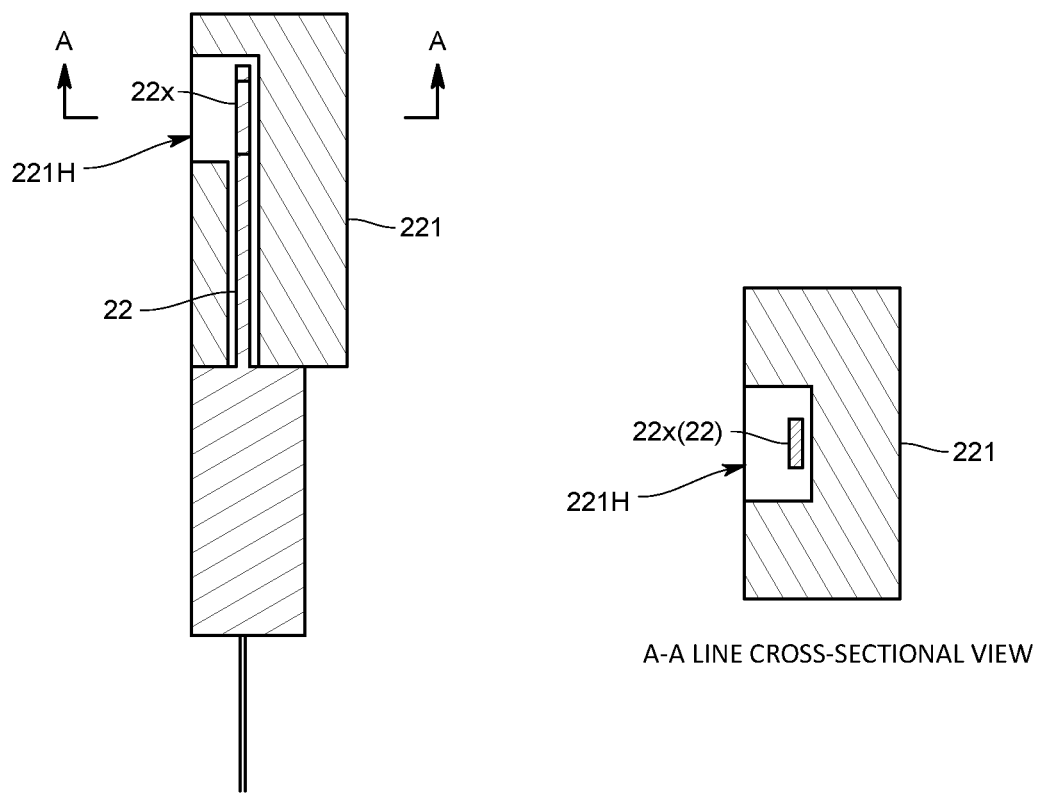
FIG. 10 is a cross-sectional view illustrating a variation of a light source.

In addition, as illustrated in FIG. 10, a heat insulating member 221 may be provided around the light source 22 of the analysis mechanism 2 in the above embodiment. The heat insulating member 221 has an opening part 221H of, for example, a columnar shape corresponding to a light emitting part 22x of, for example, a ceramic light source as the light source 22. By providing the heat insulating member 221 around the light source 22 as described, the light source 22 can be made unlikely to be affected by heat from outside, and also the light emitted from the light source 22 can be adjusted depending on the shape of the opening part 221H.

Besides, various combinations and modifications of the embodiment and variations may be made without departing from the scope of the present invention.

REFERENCE SIGNS LIST

200: Analyzer
100: Multireflection cell
11: Cell main body
MR: Multireflection mechanism
12: Field mirror
13: First objective mirror
14: Second objective mirror
IP: Light incident port
OP: Light emitting port
SP: Symmetry plane

What is claimed is:

1. A multireflection cell comprising:
a multireflection mechanism including
   a field mirror defining
      a light incident port adapted to introduce incident light into the multireflection mechanism, wherein the multireflection mechanism is adapted to multiply the incident light reflected therein to generate multiplied reflected incident light, and
      a light emitting port adapted to emit outward the multiplied reflected incident light, wherein an arrangement interval between adjacent ones of multiple reflection points formed on a reflecting surface of the field mirror is adapted to be larger in an outer edge part of the reflecting surface than a central part,
   a first objective mirror facing the field mirror and provided on a same side of the multireflection mechanism as the light incident port, and
   a second objective mirror facing the field mirror, provided on a same side of the multireflection mechanism as the light emitting port, and adapted to first reflect the incident light.

2. The multireflection cell according to claim 1, wherein the first objective mirror and the second objective mirror are arranged symmetrically with respect to a symmetry plane including a light axis of the field mirror.

3. The multireflection cell according to claim 1, wherein a curvature center of the first objective mirror is set on the same side of the multireflection mechanism as the light emitting port; and
a curvature center of the second objective mirror is set on the same side of the multireflection mechanism as the light incident port.

4. The multireflection cell according to claim 1, wherein an array of multiple reflection points formed on a reflecting surface of the first objective mirror and an array of multiple reflection points formed on a reflecting surface of the second objective mirror respectively form parabolas having respective vertices that face outward from the multireflection mechanism.

5. The multireflection cell according to claim 1, comprising
a cell main body adapted to contain the multireflection mechanism, wherein
on a side of the field mirror in the cell main body, an incident window allowing the light to be incident into the multireflection mechanism from outside and an emitting window allowing the light to be emitted outward from the multireflection mechanism are provided,
a face plate part of the incident window is orthogonal to a light axis of the incident light and faces a side of the second objective mirror, and
a face plate part of the emitting window is orthogonal to a light axis of the emitted light and faces a side of the first objective mirror.

6. The multireflection cell according to claim 1, comprising
a cell main body adapted to contain the multireflection mechanism, wherein
on a side of the field mirror in the cell main body, an incident window allowing the light to be incident into the multireflection mechanism from outside and an emitting window allowing the light to be emitted outward from the multireflection mechanism are provided, and
on surfaces of the incident window and the emitting window, an antireflection film is formed.

7. An analyzer comprising the multireflection cell according to claim 1.

8. An exhaust gas analyzer comprising:
the multireflection cell according to claim 1, wherein
exhaust gas is configured to exist between the field mirror, and the first objective mirror and the second objective mirror.

9. A light incident method making light incident into a multireflection mechanism that includes (i) a field mirror defining a light incident port adapted to introduce incident light into the multireflection mechanism, wherein the multireflection mechanism is adapted to multiply the incident light reflected therein to generate multiplied reflected incident light, and a light emitting port adapted to emit outward the multiplied reflected incident light, (ii) a first objective mirror facing the field mirror and provided on a same side of the multireflection mechanism as the light emitting port, and (iii) a second objective mirror facing the field mirror and provided on a same side of the multireflection mechanism as the light emitting port, the light incident method comprising:
making the light incident into the multireflection mechanism such that the incident light is first reflected by the second objective mirror; and
making an arrangement interval between adjacent ones of multiple reflection points formed on a reflecting surface of the field mirror larger in an outer edge part of the reflecting surface than a central part.

* * * * *